United States Patent [19]

Schroeder et al.

[11] Patent Number: 5,359,511

[45] Date of Patent: Oct. 25, 1994

[54] METHOD AND APPARATUS FOR OBTAINING COORDINATES DESCRIBING THREE-DIMENSIONAL OBJECTS OF COMPLEX AND UNIQUE GEOMETRY USING A SAMPLING PROBE

[75] Inventors: William Schroeder, Wayland; William K. Kendrick, Jamaica Plain; Bruce Nappi, Reading, all of Mass.

[73] Assignee: Foster-Miller, Inc., Waltham, Mass.

[21] Appl. No.: 163,012

[22] Filed: Dec. 6, 1993

Related U.S. Application Data

[63] Continuation of Ser. No. 862,980, Apr. 3, 1992, abandoned.

[51] Int. Cl.⁵ .............................................. G06F 15/42
[52] U.S. Cl. ............................ 364/413.28; 364/474.05
[58] Field of Search ...................... 364/413.28, 474.05; 356/376; 433/223

[56] References Cited

U.S. PATENT DOCUMENTS

| 1,387,329 | 8/1921 | Stark . | |
|---|---|---|---|
| 3,727,119 | 4/1973 | Stanley et al. | 318/568 |
| 4,182,312 | 1/1980 | Mushabac | 433/68 |
| 4,575,805 | 3/1986 | Moermann et al. | 364/474 |
| 4,611,288 | 9/1986 | Duret et al. | 364/474 |
| 4,663,720 | 5/1987 | Duret et al. | 364/474 |
| 4,837,732 | 6/1989 | Brandestini et al. | 364/413.28 |
| 4,997,369 | 3/1991 | Shafir | 433/72 |
| 5,017,139 | 5/1991 | Mushabac | 433/108 |
| 5,027,281 | 6/1991 | Rekow et al. | 364/474.24 |
| 5,121,334 | 6/1992 | Riley et al. | 364/474.05 |
| 5,128,870 | 7/1992 | Erdman et al. | 364/474.05 |
| 5,144,753 | 9/1992 | Murphy | 33/514 |
| 5,224,049 | 6/1993 | Mushabac | 364/474.05 |

FOREIGN PATENT DOCUMENTS

| 0040165 | 11/1981 | European Pat. Off. . | |
|---|---|---|---|
| 0091876 | 10/1983 | European Pat. Off. . | |
| 0110797 | 6/1984 | European Pat. Off. . | |
| 0386271 | 9/1989 | European Pat. Off. . | |
| 0369891 | 11/1989 | European Pat. Off. . | |
| 1194061 | 11/1959 | France . | |
| 75885 | 7/1961 | France . | |
| 2081697 | 3/1971 | France . | |
| 157456 | 1/1962 | U.S.S.R. . | |
| 1319561 | 6/1973 | United Kingdom . | |
| 2140308A | 11/1984 | United Kingdom | A61C 19/00 |

OTHER PUBLICATIONS

Brochure, "DCS-Titansystem Dux 1", Gim-Alldent, Germany.
Brochure, "Announcement–Procera Station Installed", Nobelpharma, Feb. 1991.
Matts Anderson et al., "Clinical results with titanium crowns fabricated with machine duplication and spark erosion", Acta Odontal Scand 47, pp. 279–286 (1989).
Brochure, "Capture 3-Dimensinoal Position Data Instantly From Any Object–The Perceptor", Micro Control Systems, Inc.
Rekow, E. Dianne, "Dental CAD-CAM Systems–What is the State of the Art?" JADA, vol. 122, Dec. 1991, pp. 43–48.

Primary Examiner—Roy N. Envall, Jr.
Assistant Examiner—Ari M. Bai
Attorney, Agent, or Firm—Wolf, Greenfield & Sacks

[57] ABSTRACT

A data processing system and method obtains a three dimensional representation of an object with complex and unique geometry, using a sampling probe having a tip for tracing the surface of the object. Electrical signals are received which are indicative of the position of the tip of the probe. An origin is determined with reference to the object. A plurality of distances, each distance corresponding to a given direction from the origin, is stored in a device addressable by the given direction to store and to retrieve a corresponding distance. The direction and distance of the probe tip with reference to the origin in response to a received signal. The determined distance is compared to any stored distance corresponding to the determined direction. The determined distance is stored when it is less than any stored distance. The probe tip position may be displayed as a projection on a reference surface which surrounds the origin.

31 Claims, 11 Drawing Sheets

METHOD AND APPARATUS FOR OBTAINING COORDINATES DESCRIBING THREE-DIMENSIONAL OBJECTS OF COMPLEX AND UNIQUE GEOMETRY USING A SAMPLING PROBE

STATEMENT AS TO RIGHTS TO INVENTIONS MADE UNDER FEDERALLY SPONSORED RESEARCH AND DEVELOPMENT

United States has certain rights in this invention under terms of grant number 5R44DEO7835-02 awarded by the National Institute of Dental Research (National Institutes of Health).

CROSS REFERENCE TO RELATED APPLICATIONS

This application is a continuation of application Ser. No. 07/862,980 filed Apr. 3, 1992, now abandoned.

This application which claims the benefit, as a continuation-in-part under 35 U.S.C. §120 of, and is related to, U.S. patent application Ser. No. 07/682,001 (Marinaccio et al.) filed Apr. 8, 1991, now U.S. Pat. No. 5,131,844 issued Jul. 21, 1992 which is expressly incorporated by reference herein.

FIELD OF THE INVENTION

The present invention relates to a data processing system which receives data representative of a position of a probe which is traced over a surface of an object. The system determines from this data coordinates describing the surface of the object. The system may be used, for example, for digitizing dental surfaces, either within the oral cavity, or outside the oral cavity, for example in the dental laboratory. The system may also be used in conjunction with suitable computer modeling systems and computer-aided design systems. In particular, the system may be used in connection with, for instance, dental applications, such as orthodontics, prosthodontics, other restorative dentistry and teaching.

BACKGROUND OF THE INVENTION

Three dimensional digitizing devices, which obtain a representation of the surface of an object, are used in a variety of fields. In particular, such devices are commonly used in areas requiring computer modeling and computer-aided design of objects. These digitizers may be used to replace techniques such as casting which typically are less accurate and require significant time and expertise to perform.

Three dimensional digitizing devices may be divided roughly into four areas: mechanical contact, magnetic, ultrasonic and digital imaging. In the dental field, commercially available systems for computer-aided fabrication of dental restorations utilize either mechanical contact or digital imaging digitizing devices. These commercially available systems are described and compared in "Dental CAD-CAM Systems-What is the state of the art?" JADA, vol. 122, December 1991, pages 43–48, by E. Dianne Rekow. Another commercial system, though not suitable for use in a dental environment, is a mechanical contact, three-dimensional digitizer called the Space Tablet and the Perceptor 3D, introduced by Micro Control Systems (Vernon, Conn.).

A number of other digitizing systems were referred to in the related application Ser. No. 07/682,001 now U.S. Pat. No. 5,131,844 issued Jul. 21, 1992. Additional systems of background interest are also disclosed in U.S. Pat. Nos. 5,017,139 (Mushabac) and 4,997,369 (Shafir). See also U.K. Patent Application No. 2,140,308A.

Mechanical systems are typically advantageous over optical systems because of their relative simplicity, and hence reduced cost. However, all of the aforementioned mechanical contact systems face the problem of determining when the contact digitizer is, in fact, in contact with the surface of the sampled object. To solve this problem, most systems rely on additional electronic circuitry or mechanical structure as part of the contact digitizer to insure that any points obtained are in fact on the surface of the sampled object. For example, the "DentiCAD System" as described in the aforementioned article by Rekow, relies on having a bias current flowing through the tooth, or sampled object, when the object is being sampled. Current flows only when the probe tip is in contact with the surface of the tooth. As another example, Shafir (U.S. Pat. No. 4,997,369) relies on a Wheatstone bridge and a supplemental computer program to determine whether the object is in fact in contact with the probe tip.

Accordingly, it is an object of the present invention to provide a system and method for obtaining a digitized representation of a surface of an object using a mechanical contact probe without the need for additional circuitry or mechanical structure.

It is another object of the invention to provide a system and method for guiding an operator through the process of sampling an object.

SUMMARY OF THE INVENTION

A data processing system and method in accordance with the present invention obtains coordinates providing a three dimensional representation of an object with complex and unique geometry, using a sampling probe having a tip for tracing the surface of the object. Electrical signals indicative of the position of the tip of the probe are received. An origin, with reference to the object, is established to which sampled points may be compared.

In one embodiment of the invention, a plurality of distances, each distance corresponding to a given direction from the origin, are stored in a storage device which is addressable by a given direction to store and to retrieve the corresponding distance. The direction and distance of the probe tip with reference to the origin may be determined for a signal received. The determined distance may be compared to any stored distance corresponding to the determined direction. The determined distance may be stored when it is less than any previously stored corresponding distance.

In another embodiment of the invention, the probe tip position, as projected on a reference surface which surrounds the origin, may be displayed for the purpose of guiding an operator. The reference surface may be divided into a number of regions and sectors which are used to determine the adequacy of sampling.

Both of the foregoing embodiments may be combined into one system. The foregoing embodiments include a number of features which are improvements over the prior art. First, error rejection procedures determine whether a data point is on the surface of an object. Second, the operator is guided by a display in a manner that: sufficient accuracy is maintained to meet predetermined tolerances; sampled points are evenly distributed over the surface of the object; critical areas of the object are not neglected; and the operator is guided to complete an adequate sample as rapidly as possible.

Error rejection procedures include determining whether a point is within some minimum and maximum coordinate values, comparing the sampled point to neighboring sampled points, and maintaining the least distance in any given direction from the established origin for the object.

To provide a display to guide the operator during sampling, a reference surface is defined about the object, which may be projected graphically onto a two dimensional display. Sampled points may be projected onto this surface for the purpose of displaying the probe tip location to the user. The reference surface is divided into a number of regions and sectors which are used to determine adequacy of sampling and to communicate this determination to the user via the display. For each region, a sum of all distances obtained for points within each sector is maintained. As sampling proceeds, this sum decreases, but the rate of change of the decrease also decreases. When the rate of change is sufficiently low, sampling is sufficient. These procedures also provide a measure of the accuracy of the match of the sampled point set to the surface of the object, so that sampling can be terminated as soon as it is determined that the set of sample points is good enough to replicate accurately the sampled surface.

This data processing system and method may be used to obtain coordinates providing a three-dimensional representation of an object to develop mating objects or to copy the object. It is particularly applicable to restorative dentistry.

For a specific embodiment of the invention, an application program was developed to be used in conjunction with a 16-bit analog-to-digital converter and an IBM-PC compatible machine running in 32-bit mode. This application program is used to translate 16-bit data to 32-bit data and includes modules for retrieving data from the analog-to-digital converter and placing the retrieved data on a stack in a memory of the computer. It also includes another module which reads data off the stack as 32-bit data.

DETAILED DESCRIPTION

Figure 1:
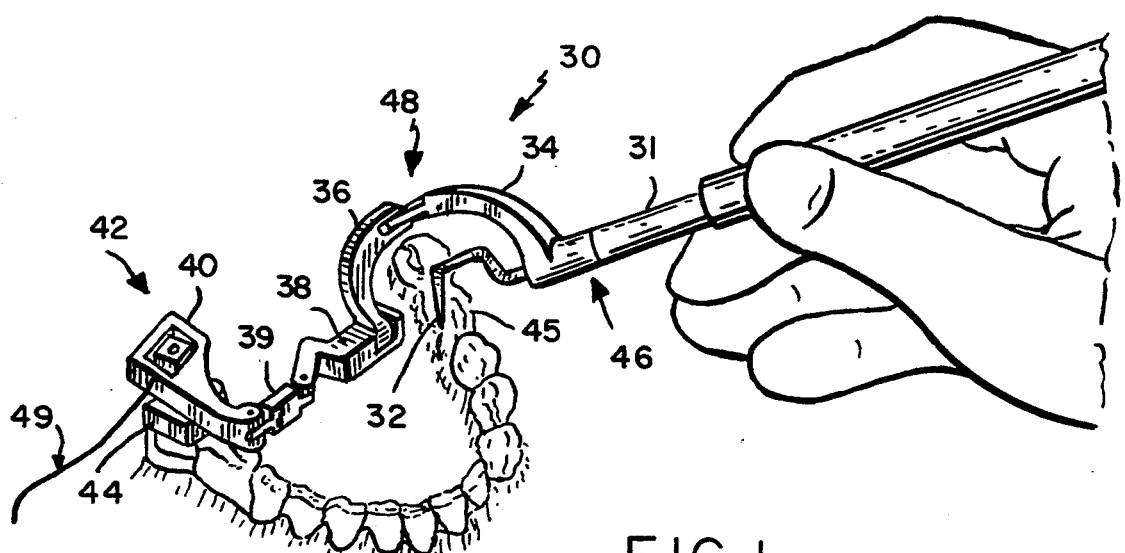
FIG. 1 is a perspective view of a typical probe which may be used in connection with the prevent invention.

A detailed description of embodiments of the invention will now be provided. This description should be read in conjunction with the accompanying drawing in which similar reference numerals indicate similar structures.

A system in accordance with the present invention may utilize a probe 30 (FIG. 1), which has a handle 31 and a tip 32 for tracing the surface of an object. Since the probe for this embodiment, shown in FIG. 1, is described in detail in the aforementioned U.S. patent application Ser. No. 07/682,001, now U.S. Pat. No. 5,131,844 issued Jul. 21, 1992 a detailed description of this probe is omitted. Further, many other types of probes may be used in connection with the system of the present invention, an appropriate probe providing an electrical signal indicative of probe tip position. This signal is typically provided by a number of sensors which sense the state of various parts of the probe. Such probes are calibrated, using known techniques, to a reference coordinate system in which the tip position is provided.

The probe of FIG. 1 is comprised of a number of linkages 34, 36, 38, 39 and 40, which are interconnected at a number of joints. One joint 42 connects linkage 40 to a base 44 which is in a fixed spatial relationship with the object being sampled. In this example, the base is attached to a tooth of a patient which is in a fixed spatial relationship with the tooth 45 which is being sampled. Joint 42 and at least two other joints, for example joints 46 and 48, are provided with sensors which provide an electrical signal which is indicative of the state, or angle, of the joint.

The type of sensor used in a probe may be selected according to a number of criteria, such as cost, type of output, linearity of output, size, precision and complexity. The probe disclosed in U.S. patent application Ser. No. 07/682,001 now U.S. Pat. No. 5,131,844 issued Jul. 21, 1992 uses Hall effect sensors. Such a sensor senses the angle of the linkage and provides an analog, non-linear output. These sensors are particularly advantageous where the probe must be miniaturized, such as in dental applications.

Resistive sensors such as potentiometers may also be used. Their advantages are their low cost and linearity of output. Their primary disadvantages are a high torque, a shorter wear life, and that they are not easily miniaturized.

Capacitive sensors may also be used. These analog, non-linear devices are inexpensive and may be easily miniaturized, but require complex external circuitry. They are very sensitive to external electronic effects, and therefore must be shielded.

Angular resolvers, which are magnetic transformer devices, are particularly useful in systems which do not require a miniaturized probe. These sensors are inexpensive and have been used substantially throughout industry. The output of such a sensor is analog and non-linear (sinusoidal).

Another type of sensor which may be used is an optical encoder. At present, these devices are not available in miniaturized form and are costly. However, they are advantageous due to their high precision and linear digital output. Thus, where cost and size are not a factor, optical encoders are particularly useful.

The output of a probe 30, regardless of the type of probe used, is provided to a system for processing via, for an example, cable 49. When the probe is appropriately calibrated to a reference coordinate system, the output of the probe may be interpreted as an indication of the position of the probe tip 32 in the reference coordinate system with respect to the base 44, or other origin location of the reference system. This position may be represented, for example, in Cartesian (x, y, z) coordinates or in spherical (R, $\theta 1$, $\theta 2$) coordinates.

When a computer system is provided with a sequence of electrical signals which represent the probe tip position in a reference coordinate system, one problem remaining to be solved is determining whether the points in the sequence of signals are on the surface of the sampled object. The system also should guide the person sampling the object and assist in determining whether sufficient sample points have been obtained.

Figure 2:
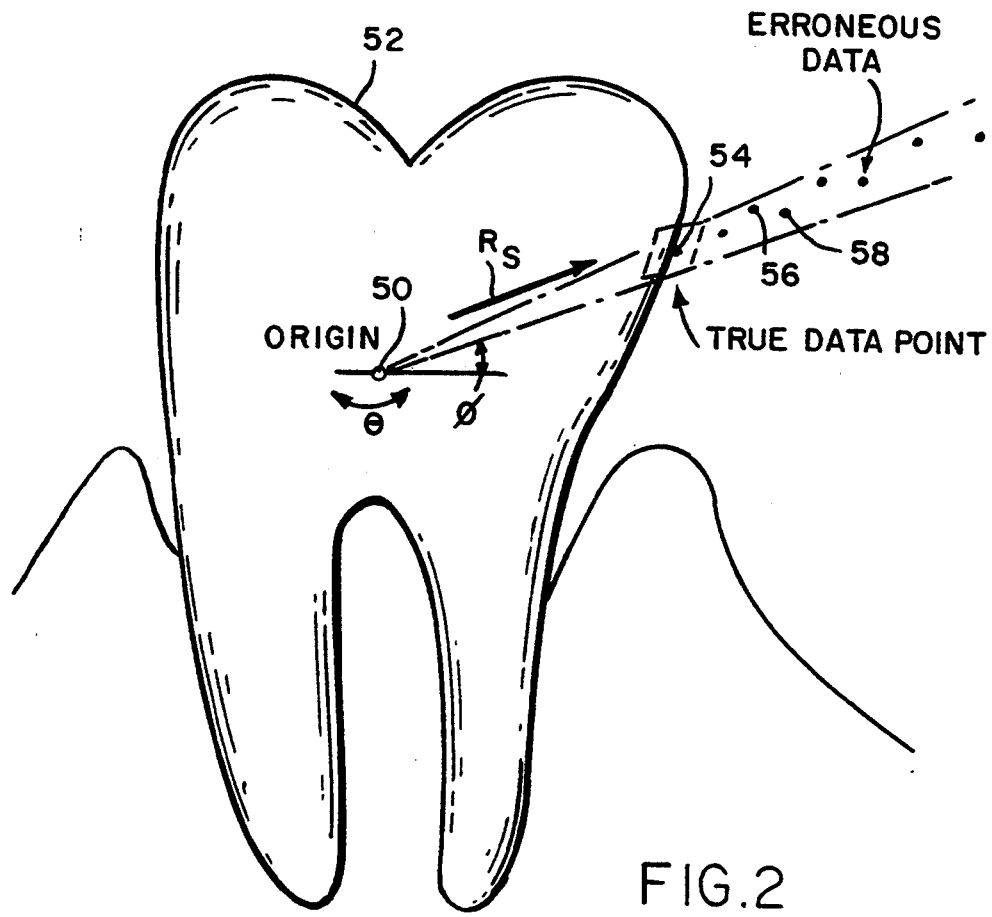
FIG. 2 is a diagram of the solution to the problem of identifying acceptable sample points in connection with the present invention.

FIG. 2 illustrates graphically a solution to the problem of determining whether a point is acceptable, the illustration being in connection with sampling of a tooth. In general, an origin 50 is selected with reference to the sampled object 52. The origin is selected such that any point 54 on the surface of the object in a given direction $\theta,\Phi$ is a distance $R_s$ from the origin which is shorter than the distance to any point in the same direction which is off the surface (i.e. points 56, 58, etc.). Many points may, in fact, be suitable as an origin. In accordance with the invention, for any given direction from the origin towards the sample surface of the object, the sample point having the shortest distance is kept as the "true data point". Other "erroneous data points" in the same direction are rejected. Using this solution, the size of a set of sample points is constant for a sampled object. The set of sample points may be stored and manipulated on a computer to implement this solution and to guide a user in the sampling process by indicating the adequacy of the sample data and by indicating the location of the probe tip.

Figure 3:
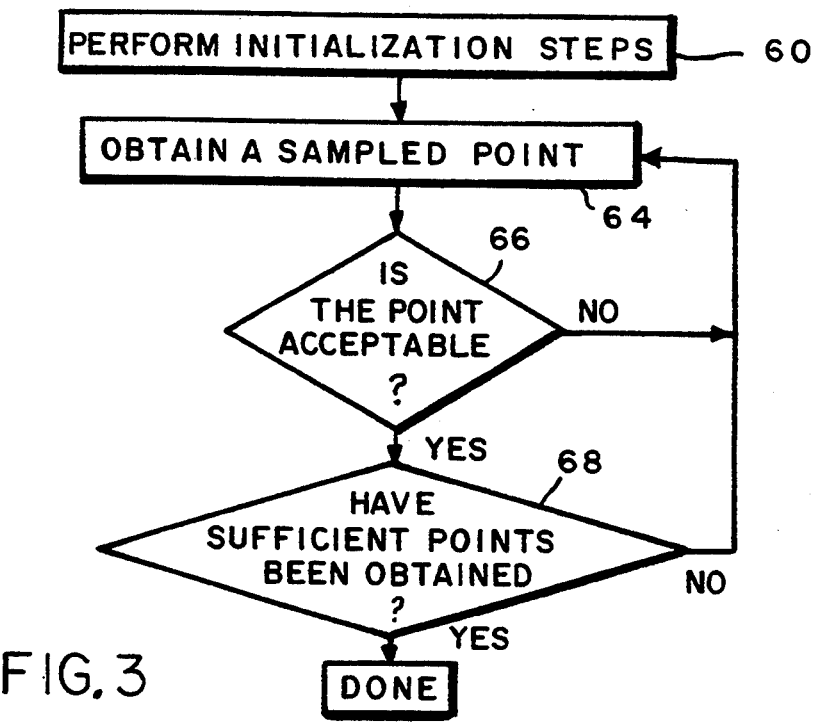
FIG. 3 is a flowchart describing a process for implementing the solution of FIG. 2 to obtain a digitized representation of an object.

The flowchart of FIG. 3 describes generally a process which implements the solution described above. The first step of this process is step 60 of performing initialization steps. For instance, an origin is selected with respect to the surface of the sampled object. This and other initialization steps will be described in further detail below in connection with FIGS. 6 through 9.

When an origin has been selected, and other initialization steps have been performed, points may be sampled, which points represent the probe tip position. For each sample point obtained in step 64, it is first determined in step 66 whether the sample point is acceptable. This process will be described in more detail below in connection with FIGS. 10-11. Generally speaking, a point is acceptable if it has a shorter distance from the origin than any previously obtained point in the same direction, as described above. If the sample point is not acceptable, it is rejected and a new sample point is obtained in step 64. If the sample point is an improvement, it is next determined whether the obtained sampling points adequately match the surface of the object being sampled (step 68). This step will be described in more detail below in connection with FIGS. 12-18. If the set of sample points is inadequate, more sample points are obtained by returning to step 64. If sufficient points have been obtained, the process of sampling may be terminated. The sampling process may also include displaying of the probe tip position to a user. The probe tip position should also be displayed when the point is not accepted. Such display procedures will be described below in more detail in connection with FIGS. 12-18.

Figure 4:
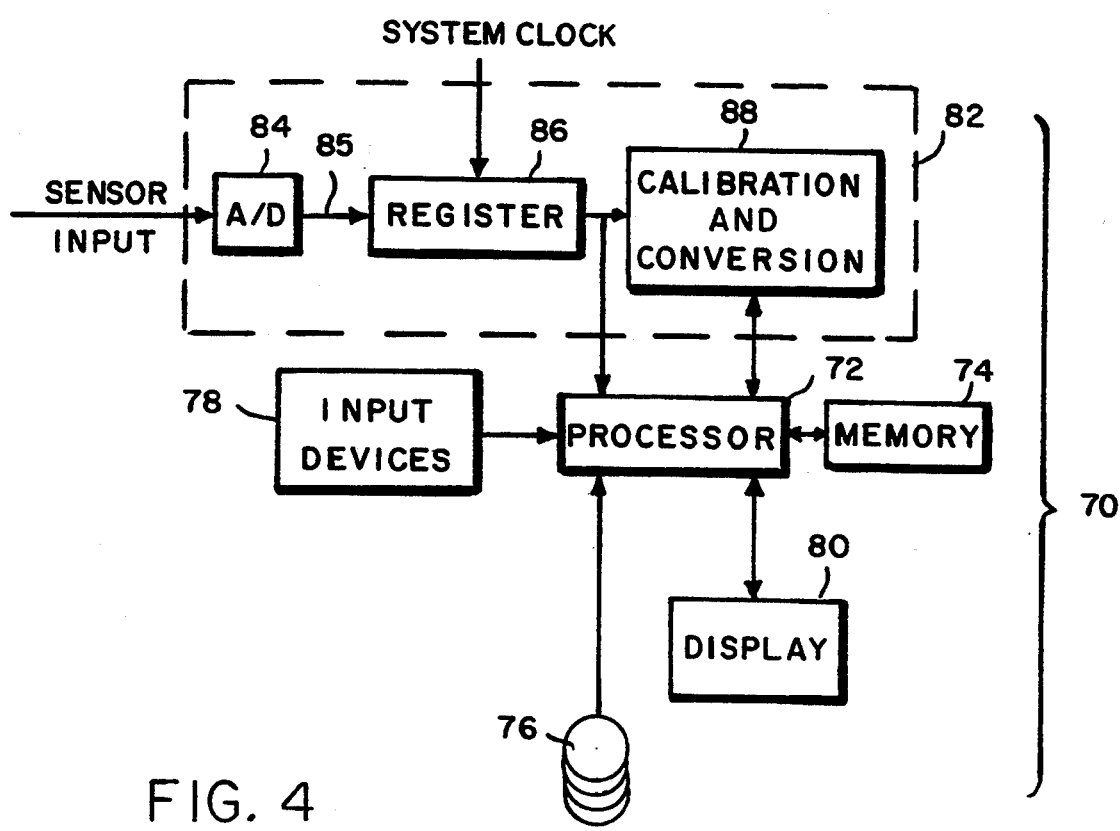
FIG. 4 is a block diagram of a data processing system which may be used in connection with the present invention.

A system implementing the above-described solution will now be described in connection with FIGS. 4-20. FIG. 4 is a block diagram of a data processing system 70 in accordance with the present invention. This data processing system may be a programmed general purpose computer, such as an IBM-PC, or special purpose hardware. Many types of general purpose computers may be used; the present invention is not limited to those mentioned. Mainframes, workstations and personal computers are all suitable for this application. The function of the system of the invention is described below in connection with flowcharts. These flowcharts will enable a computer system designer to make and use a system embodying this invention by either programming a general purpose computer and/or constructing special purpose hardware.

The data processing system 70 of FIG. 4 includes a central processor 72 which controls data flow and data manipulation in response to program steps and other inputs. The system also includes a primary memory 74 and a secondary memory 76 for storing data and application programs to be used and executed by the computer 70. Memory 74 is typically a volatile, random access memory. Data and programs are temporarily stored in this memory for manipulation or execution. The secondary memory 76 is typically a hard disk, floppy disk drive or other permanent storage medium on which information and application programs may be permanently stored.

A program for the computer 70 is typically generated using well known methods and is stored in a secondary memory 76. When the computer executes a program, the program typically is loaded into primary memory 74 and its steps are executed by a processor 72. Such steps may include data manipulation and comparison, retrieval of input from a variety of input sources, and display of information to a user. The processor also controls the timing of the computer system 70 and control of a number of input and output devices 78 and 80, described below.

The data processing system 70 also includes a number of input devices 78. For an input device, the data processing system 70 may include a keyboard, mouse system, voice recognition system, buttons, and a variety of other media. Such input devices 78 provide a series of electrical pulses indicative of their state. These electrical pulses are sent to the central processor unit 72 for evaluation.

The data processing system 70 also may include output devices, such as a display 80 for providing a readable output to a user. Such output devices convert electrical pulses sent from the central processor 72, which are indicative of specific characters, which electrical pulses are then converted into other signals, either visual or audio, which may be interpreted by a user. Such devices typically include television screens, voice or audio synthesizers, and similar devices. In connection with the sampling operation involved with the present invention, a color television screen having sufficient resolution should be used for optimum results. A similar display with a sufficient grey scale may also be used.

The computer system 70 also includes a probe input system 82 which receives electrical signals from a probe, as described above, and provides a digital signal indicative of the probe position in some reference coordinate system to the processor 72. The probe input system 82 includes an analog-to-digital (A/D) converter 84 to convert analog signals from a probe into digital signals which may be used by the computer system 70. A suitable A/D converter is a conventional plug-in A/D board for an IBM-compatible personal computer, such as the DATA TRANSLATION DT2808. Other A/D converters may also be used as should be evident to those skilled in the art. The A/D converter 84 is not required for probes which provide digital signals. Because an A/D converter 84 typically operates with a sampling rate which is different than the rate at which the computer system 70 operates, the output of the A/D converter 85 is received by a register 86 which operates at a rate defined by the "system clock" which is the rate at which the computer system 70 is operating. The system clock rate typically ranges from 16 to 33 Mhz.

The signals from the probe may be provided directly to the processor 72 or may be converted by a calibration and conversion processor 88. The calibration and conversion processor 88 may be implemented in special purpose hardware, or as an application program, (in which case processor 88 is a series of memory locations) in the form of a lookup table or a polynomial function. The calibration and conversion processor 88 converts the digital signal obtained from the probe into coordinate values in a spatial reference coordinate system, such as spherical (R, $\Theta_1$, $\Theta_2$) or Cartesian coordinates (x, y, z), which the computer system 70 is programmed to recognize. The contents of processor 88 are defined during calibration of the probe. If this processor 88 is implementing a polynomial function, it is typically implemented as a computer program which is executed by the processor 72. When implemented as a lookup table, the calibration and conversion processor 88 may be implemented with a memory, such as a programmable read only memory, or a non-volatile memory. It may also be stored on a non-volatile memory device, such as on a secondary memory 76, and then loaded into a faster volatile memory when needed. The probe input system may also receive other input signals from other analog, typically non-standard, input devices. For example, a foot pedal may provide an analog signal when depressed which may be received by the analog-to-digital converter, and thus provide a digital signal representing the state of the foot pedal to the processor 72. Such an arrangement is useful when a desired input device cannot be adapted to fit the typical input device format required by the specific computer used for input devices 78.

Typically, the analog-to-digital converter 84 (FIG. 4) provides a 16-bit output. In an embodiment of the present invention, now described in more detail in connection with FIG. 5, a 16-bit analog-to-digital converter 200 made by DATA TRANSLATION (DT2808) was used as mentioned above. The A/D converter 200 was used in conjunction with an IBM-PC, with an INTEL 80386 processor. An application program implementing the procedures described in this application was developed to run on this computer in a 32-bit mode. It should be understood that many other different types of general purpose computers could be used to implement the present invention, the embodiment described being merely an example of the present invention. With this embodiment, however, another application program, known as a driver, was developed to translate data from the 16-bit analog-to-digital converter to 32-bit data to be read by the application program (202 in FIG. 5). This driver will now be described in connection with FIG. 5.

Figure 5:
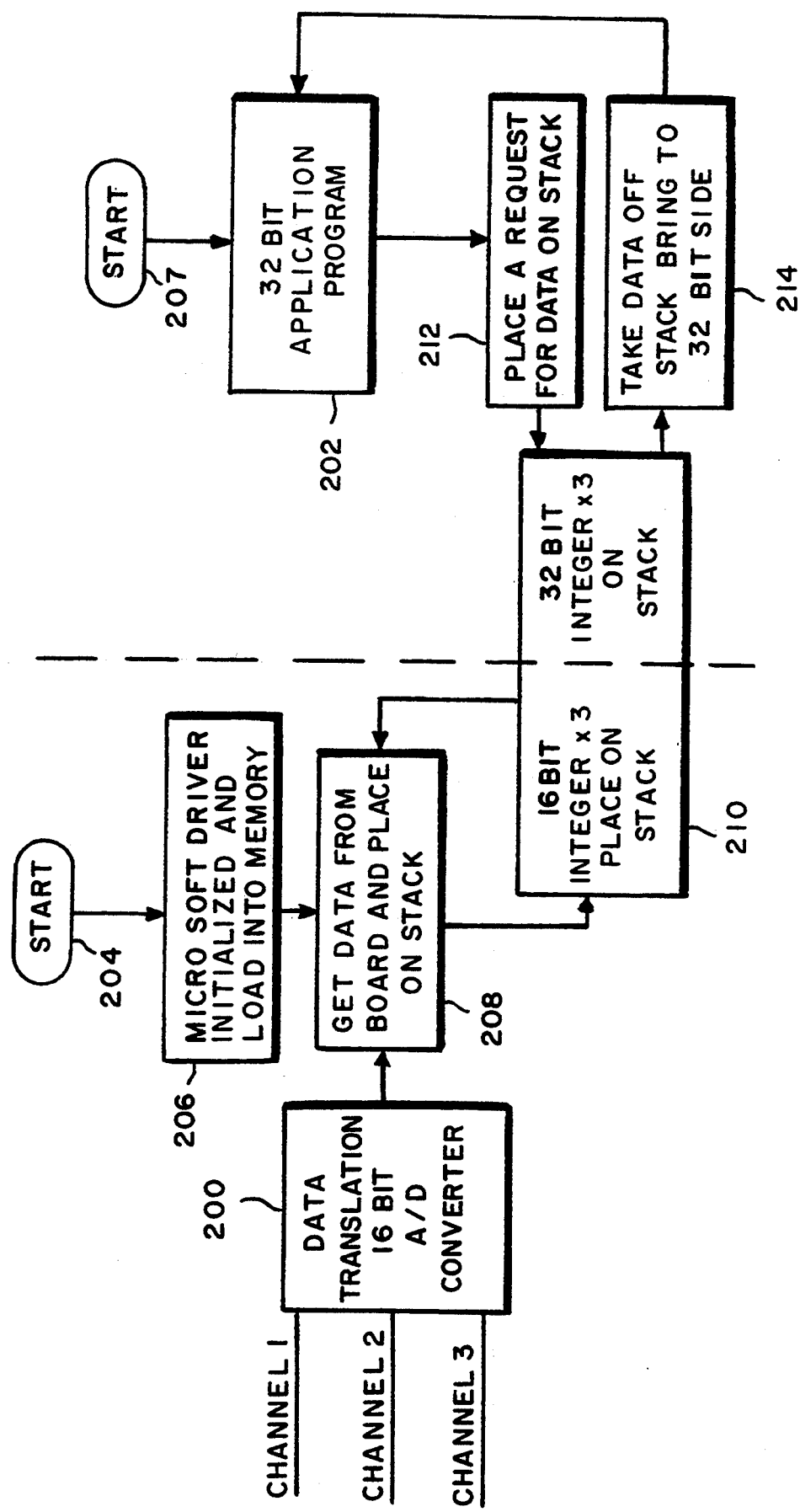
FIG. 5 is a module dependency diagram of a driver for translating 16 bit data to 32 bit data.

When the data processing system 70 is started, shown as module 204 in FIG. 5, a driver is initialized and loaded into memory 74 (block 206). This driver includes modules 208 for retrieving data from the analog-to-digital converter and placing that data on a stack 210 which is part of the memory 74. This module 208 is responsive to a request for data which may be placed on the stack 210.

When the application program 202 is started such as shown in step 207, the driver is linked to the application program to respond to requests for data and to take data from the stack 210. The driver includes a module 212 responsive to an application program for placing a request for data on the stack 210. When requested data is placed on the stack by module 208, it can be read as 32-bit data by another module 214 of the driver, which then provides the data to the application program 202.

When the driver is executed (i.e., started at run time) pointers, in both the 16-bit and 32-bit read/write modules 208 and 214, to memory locations allocated for the stack 210 are hash-defined (i.e. using a hash function) so that they point to the same memory locations. Module 208 uses its pointer simply to load a 16-bit data word into 32-bit memory location, the loaded bits being followed by 16 additional, unused bits. This data word module 214 reads 32-bits from the same location: the 16-bit data word and the 16 additional, unused bits. Typically, these additional bits contain a value which must be subtracted out to retain the value of the original 16-bit data. If the memory for the stack 210 is allocated to the driver before it is used by other programs, this value is constant.

The sampling process and system of the present invention to be implemented on data processing system 70 will now be described in connection with FIGS. 6–18. The steps of initialization will first be described in connection with FIGS. 6–9.

Figure 6:
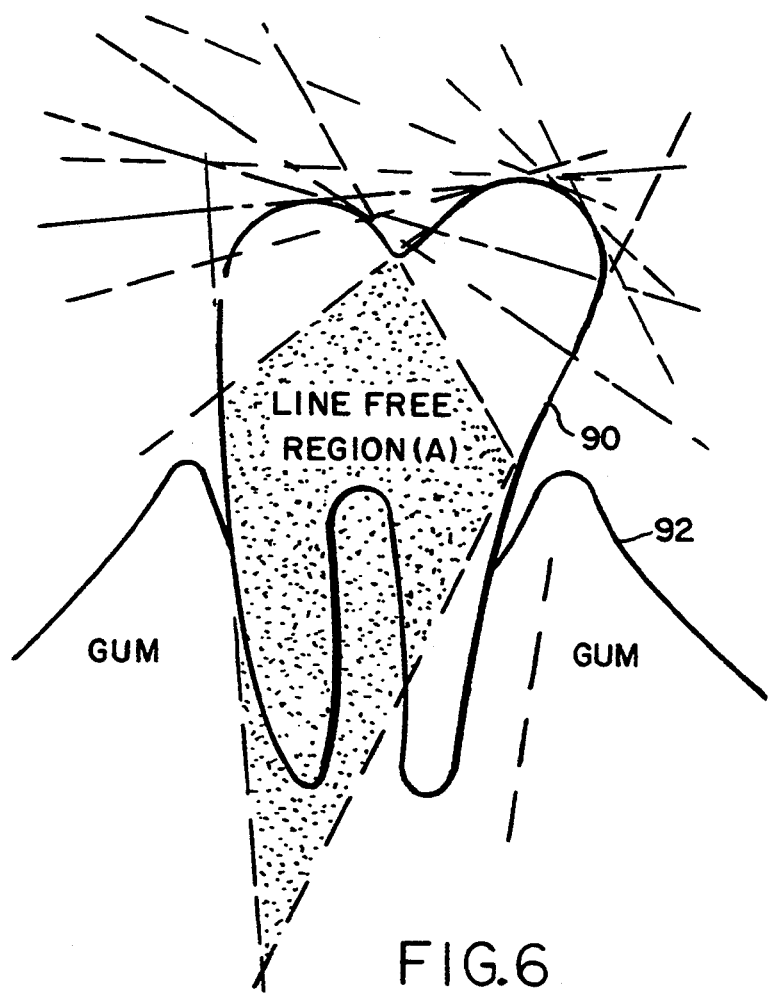
FIG. 6 is a diagram illustrating a constraint on the selection of an origin for a tooth.

FIG. 6 graphically illustrates a constraint for the selection of an origin with reference to the surface of the sampled object. In FIG. 6, a tooth 90 is being sampled. The surface to be sampled includes the exposed surface above the gum 92. Ideally, an origin should be selected such that it is located in line free region A, which is the region through which no tangent line to the sample surface passes. Generally speaking, the origin should be located so that a line through it in any point along the surface contains no other point on the surface. With these restrictions, any shape of Euler number 0 (i.e. which has no holes through it) may be digitized.

This constraint can be generalized to many other shapes in the following manner. The origin may be a set of points (either a curve or a surface). With this generalization, rather than keeping points which have a least distance to a single origin, the least distance between the sample point and the origin set is maintained. If the origin set of points is a circle, and is appropriately located, a simple ring could be sampled.

Figure 7:
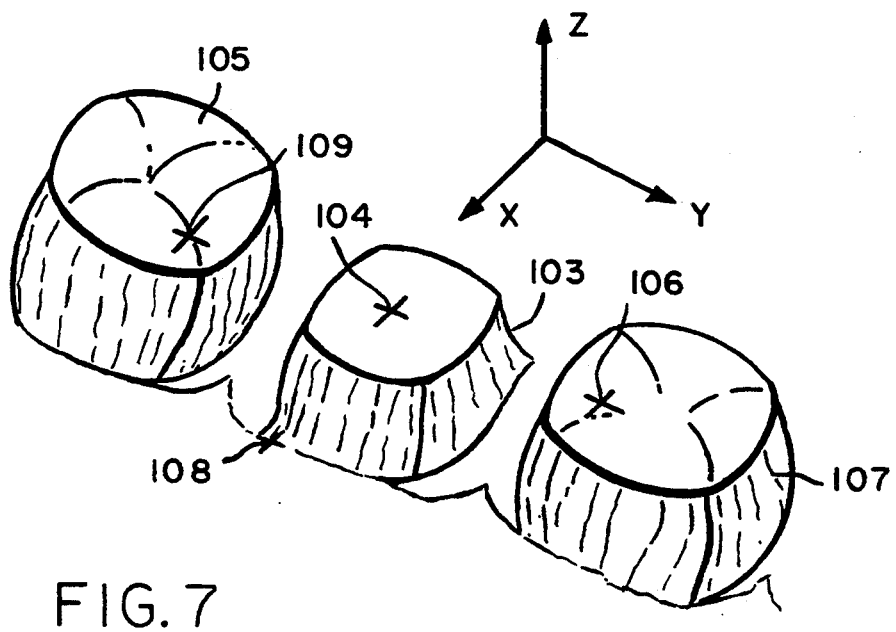
FIG. 7 is a perspective view of teeth to be sampled, indicating characteristic locations of the surface.

A method for selecting an origin with reference to the object to be sampled will now be described in further detail in connection with FIGS. 7 and 8. The origin selected has coordinates in the reference coordinate system recognized by the computer for the probe. Coordinates for sample points obtained are converted from the reference coordinate system to a coordinate system based on the selected origin on the basis of the coordinates of the selected origin. There are generally two methods for selecting an origin. The first method involves accepting data (sample points) continuously and calculating an origin as soon as sufficient sample points have been acquired. For example, a sampling probe can be placed at various locations around the tooth, and using some appropriate geometrical calculations, an origin may be determined. This first method for determining an origin is advantageous when the characteristics of the object to be sampled are relatively unknown.

Figure 8:
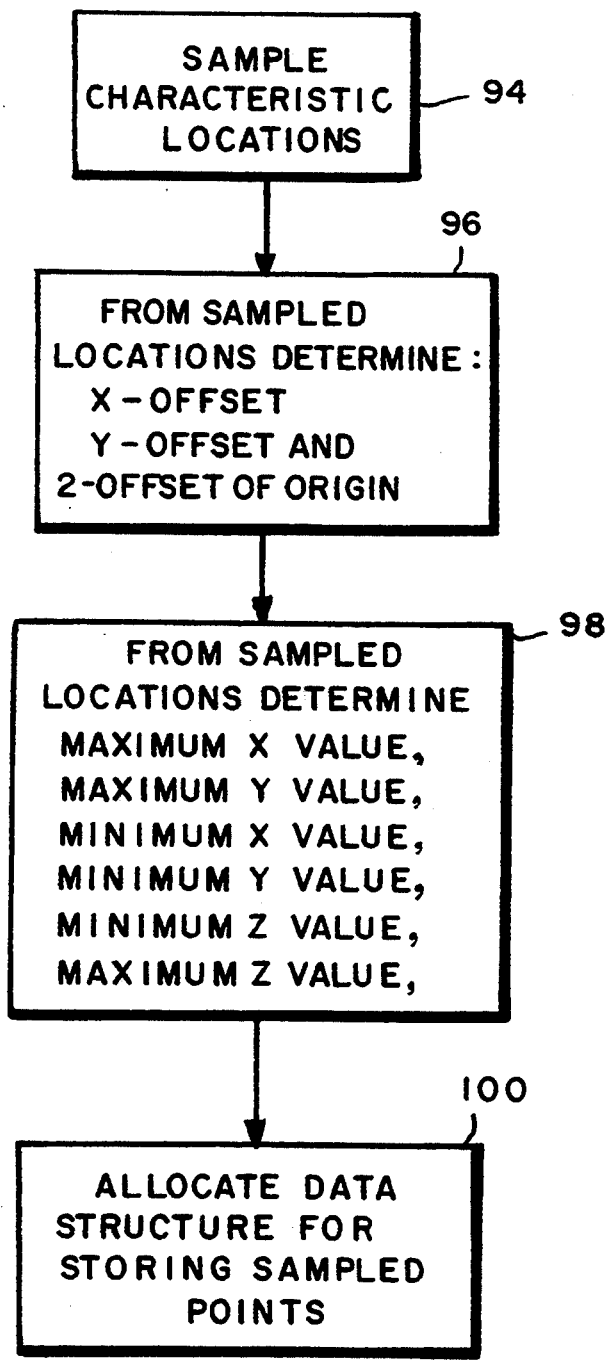
FIG. 8 is a flowchart describing how the process of sampling is initialized.

The second method, described in more detail below in connection with FIG. 8, is particularly useful if the characteristic shape of the object is known in advance. When the shape is known in advance, the location of a desired origin may also be known and may be defined by a number of characteristic locations which may be sampled using a probe. These points may also define the full extent of the object as well, i.e., its largest dimension in any direction.

As shown in FIG. 8, the first step of determining the origin for the second method is step 94 of sampling characteristic locations of the surface. Characteristic locations are locations of which at least one coordinate defines one of the origin coordinates or the extent of the object. In the example of FIG. 7, the surface to be sampled is a prep 103 for which a crown will be prepared. Typical characteristic locations in this example are the center 104 of the top of the prep 103 and the margin points such as point 108. Margin points are the lowest region of the surface of the sampled object. For a tooth, the margin is at the gum line. Only one margin point need be sampled for the purpose of determining the origin, provided that it is the lowest margin point. Typically, a number of margin points are sampled to determine the full extent of the object in the X and Y directions, and the lowest Z coordinate of the object. It should be apparent to those skilled in the art, from this example, how to determine characteristic locations for other objects of known shape.

The foregoing procedures may also be adapted for other objects of complex shape. Complex objects may be broken down into a number of sections for the purpose of sampling, if necessary. A different origin could be determined for each section of the object. Subsequently, the sampled points for each section could be combined to provide a complete representation of the object to be used for modeling or other purposes.

In order to obtain sufficient sample data for constructing a crown in dental applications, other surfaces, i.e., interproximal and occlusal surfaces, also need to be sampled. Sampling of these surfaces is performed in a manner similar to sampling of the tooth prep. For each interproximal surface, a suitable origin is located inside its corresponding tooth. (The interproximal teeth are teeth 105 and 107 in FIG. 7). Characteristic locations for the interproximal teeth may be locations 109 and 106 respectively. Other characteristic locations for the purpose of limiting sampling are points on the sides of teeth 105 and 107.

Sampling of occlusal data, generally, means obtaining data concerning a surface which is to mate with a design surface (such as an opposing tooth with a crown). In the case of the example above (FIG. 7), the mating surface is not always in contact with the surface to be designed. In order to sample this surface, an impression of the mating tooth in place is taken. That is, some amorphous material is placed over the prep, and the mouth is closed to cause the occlusal surface to be pressed against the material to make an impression. With this impression properly positioned, data for the mating surface may be obtained by digitization of the impression using the same coordinate origin as originally used to sample the prep 103. Other characteristic locations (the extent of sampling in the x and y directions, for example) are obtained by sampling a line or circle around the area of the impression which is to be sampled. The computer can use these points as reference points to limit the sampling process, as they define the full extent of the sampling region.

After characteristic locations have been sampled in step 94, the coordinates obtained for these sampled locations are used to determine the coordinates of the origin in the reference coordinate system (step 96). From the center point 104 (see FIG. 7), X and Y coordinates are taken as the X and Y coordinates of the origin. The Z coordinate of the lowest margin point sampled determines the Z coordinate of the origin: the Z coordinate of the origin is some offset below the Z coordinate of the lowest sampled point. This offset is typically a small distance, such as one or two measures of the accepted tolerance for sampling.

Also from the sampled characteristic locations, minimum and maximum values for the X, Y and Z dimensions are determined and stored in step 98. Typically the minimum Z value is the origin which is determined in step 96 as it is selected to be lower than any margin point. The maximum and minimum x, y and z values are taken as the maximum and minimum values obtained from the characteristic locations.

Steps 94, 96 and 98 need not be performed as distinct, separate, sequential steps as shown in the flowchart. These steps may be performed for each sampled characteristic location. The order of performance will depend on the particular implementation used.

Another part of the initialization procedure, which may be performed before or after obtaining an origin, involves allocating a data structure for storing sample points. This data structure is a record which stores, for each point, its X, Y and Z (Cartesian) coordinates with respect to the origin, the distance from the origin to the sample point (radius R) and its azimuth ($\Theta_1$) and elevation ($\Theta_2$) (i.e., the spherical coordinates of the point). One skilled in this art will know how to convert spherical or Cartesian coordinates in the reference coordinate system to coordinates with respect to the origin. One record is made for each azimuth/elevation combination. That is, the range of azimuth values is 360°. The range of elevation values is 180°. If the resolution of the sampling is 1°, there are 360 possible azimuth values and 180 possible elevation values. Thus, there are a little more than 64,000 possible combinations.

The azimuth and elevation represent the direction of a sample point from the origin. These values may be used to address the data structure described above, to retrieve x, y and z coordinates and the distance from the origin of any previously stored point. Given the azimuth and elevation (direction) of any new point it may be readily determined if that point is an improvement over any previously stored point. One possible implementation of these data records is a two-dimensional array addressable by the azimuth and elevation values of the sampled point.

Figure 9:
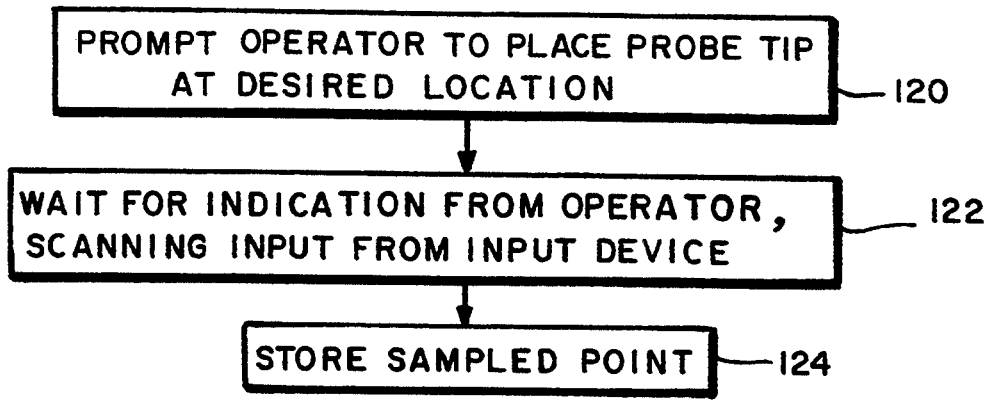
FIG. 9 is a flowchart describing how characteristic sample points are obtained.

FIG. 9 describes in more detail how specific points, such as characteristic locations, may be sampled. The data processing system 70 provides a prompt to the operator in step 120 (for instance, via display 80 or other output device) which informs the operator to place the probe tip 32 at a desired location. The data processing system 70 then waits, (step 122) until it receives an indication from an operator that the probe tip 32 is at the desired location. This step 112 assumes that the operator actually will place the probe tip 32 at the desired location. The indication from the operator may be provided via one of the input devices 78. Based on this assumption, the data processing system 70 scans the appropriate input device 78 (or A/D board 84) for such an indication. For example, the computer could periodically examine the input from the A/D converter 84 until a signal is received that indicates that a foot switch, as described above, has been depressed.

When the appropriate indication from the operator has been received by the data processing system 70, the sample point received from the sampling probe may then be stored in memory 74 at an appropriate location, for further processing (step 124).

When the foregoing procedures are completed, the coordinates of an origin have been determined, and the appropriate data structure has been allocated in memory 74 of the data processing system 70.

Figure 10:
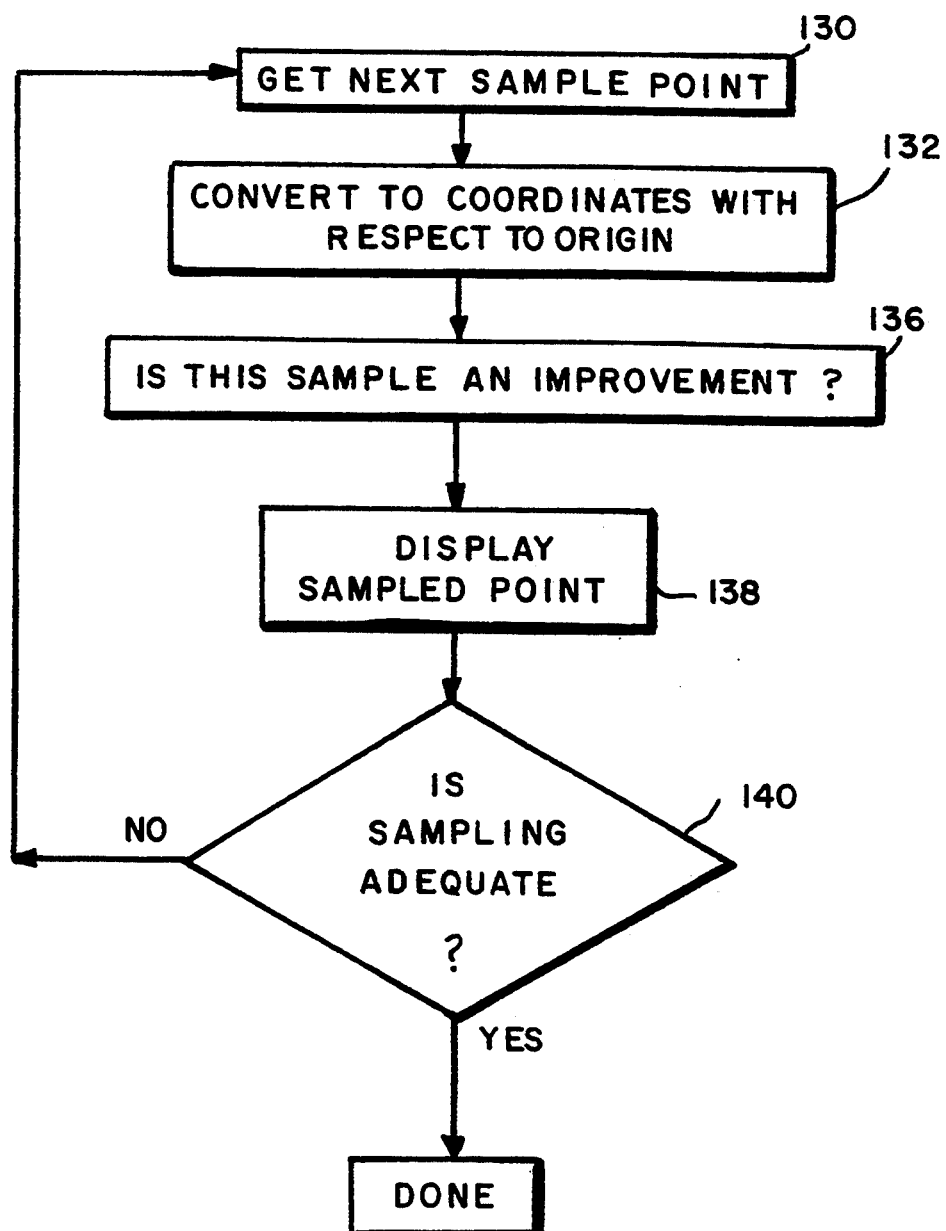
FIG. 10 is a flowchart of the general sampling process.

A method for sampling, given an origin and appropriate data structure, will now be described in connection with FIG. 10, which adds further detail to the flowchart of FIG. 3. The first step of sampling is step 130 of obtaining the next sample point. During the sampling process, after initialization is completed, an operator simply runs the tip 32 of the sampling probe around the sampled object. At this stage of sampling, the operator need not provide an indication (via an input device) to the data processing system that sampling is taking place. The data processing system may simply take the coordinates from the A/D board when needed. When a sample point is obtained, its coordinates are converted so that they refer to the determined origin for the sampled object (step 132). Appropriate calculations are made so that, for each point, Cartesian and spherical coordinates are available. Step 132 is followed by a determination of whether the new point is an improvement over any previously obtained point in the same direction from the origin (step 136). This determination will be described in more detail below in connection with FIG. 11. Generally speaking, if the sample is not an improvement, it is rejected. If the sample point is an improvement, the sample point is stored, and the previous point in the same direction rejected. The position of the probe tip 32 is then displayed on display 80 (step 138) and it is determined in step 140 whether sampling of the object has been adequately completed. Steps 138 and 140 will be described in more detail below in connection with FIGS. 12–18. If sampling has been determined to be adequate, the process of sampling is complete. Otherwise, a new sample point is obtained in step 130 and the steps of this process are repeated.

Figure 11:
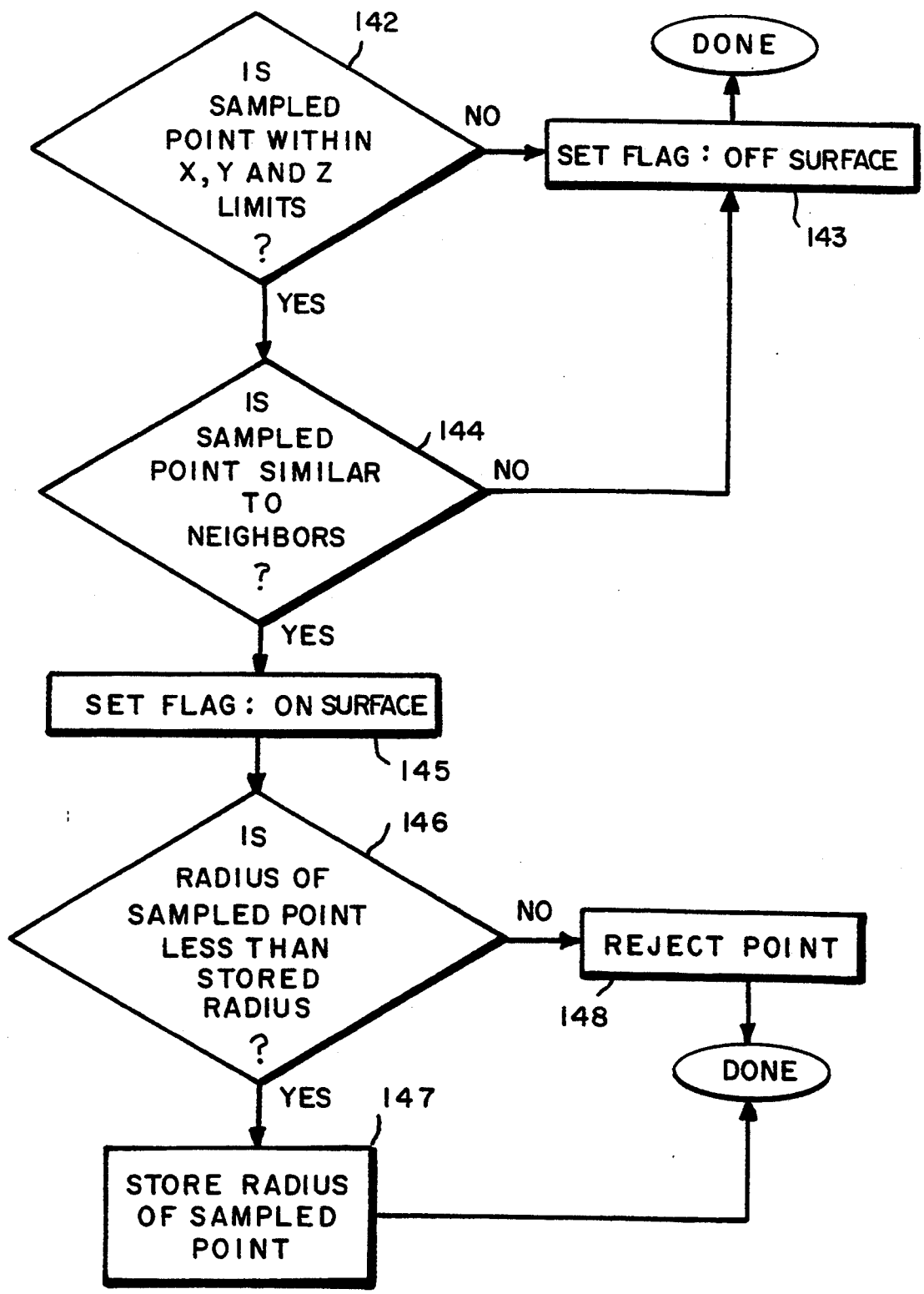
FIG. 11 is a flowchart of the process of determining whether a sample point is acceptable.

The determination of whether a point is an improvement, or is acceptable, will now be described in connection with the flowchart of FIG. 11. The first step of this procedure is step 142 of determining whether the sample point is within the maximum and minimum x, y and z coordinates established for sampling the object. These limits were determined in step 98 (FIG. 8) of initialization. If the sample point is not within these limits, it is not on the surface of the object. A "flag" may then be set, in step 143, by storing a value in memory 74, indicating that the sampled point is off the surface. This "flag" is used for display purposes. If the sampled point is within the x, y and z limits, it may then be compared to the points which have been obtained for neighboring azimuth and elevation locations (step 144). Step 144 is performed when a sufficient number of sample points have been obtained in a region containing the given sample point. A region may be defined according to azimuth values. If, for example, one percent of the possible locations within a region have sample points, this step 144 is performed. Otherwise, this step should be omitted.

Step 144 of comparing the sample point to neighboring points involves determining whether the distance from the origin obtained for the sample point is within some offset of each of the distances obtained for its neighboring points. A sample point may be compared to neighboring points in the following manner. Other methods may also be used. Given the radius R, azimuth A and elevation E of sample point, the following inequalities may be evaluated:

$$R(A/Azfactor)(E+1/Elefactor)+Criteria+-Weight> = Current\ R$$

$$R(A+1/Azfactor)(E/Elefactor)+Criteria+-Weight> = Current\ R$$

$$R(A/Azfactor)(E/Elefactor)+Criteria> = Current\ R$$

$$R(A-1/Azfactor)(Elefactor)+Criteria+-Weight> = Current\ R$$

$$R(A/Azfactor)(E+1/Elefactor)+Criteria+-Weight> = Current\ R$$

Where "azfactor" and "elefactor" are variables approximately equal to one, where "criteria" is the sum of the desired tolerance and the values of known system noise, and where "weight" is the sum of some desired offset, possibly including the dimension of the probe tip, and a constant. A typical value for the constant is 0.0345 for tooth sampling. If more of these inequalities are true than false, the point is rejected.

These inequalities, for performing step 144, may be extended to compare the sample point to more distant neighboring points. The results of evaluated inequalities may be weighted according to their distance from the sampled point. If a sufficient number of neighboring points are determined to be similar to the sampled point (step 144), the sample point is considered to be on the surface and the "flag" is set in step 145. Otherwise, it is determined that this point is likely not to be on the surface of the sampled object and it is rejected. Thus, the "flag" is set in step 143 to indicate the point is off the surface of the object. If it is determined, in steps 142 and 144, that the sample point is likely to be on the surface of the sampled object, it is then determined in step 146 whether the radius, or distance from the origin, of the sample point is less than the radius already stored for the direction indicated by the azimuth and elevation values of the point. The stored radius, or distance, is initialized to a very large value during the initialization procedure described above. Thus, the first sample point in a given direction likely will be stored in step 147. If the radius of the sample point is not less than the stored radius, the sample point is rejected. Steps 142 and 144 of determining whether the sample point is on the surface of the object are useful for preventing storage of poor data, especially in systems whose resolution is very fine. Inaccurate data will appear as spikes in the sampled data set, which are difficult to dispose of, and which create large errors in interpolation, if necessary, and modeling.

Figure 12:
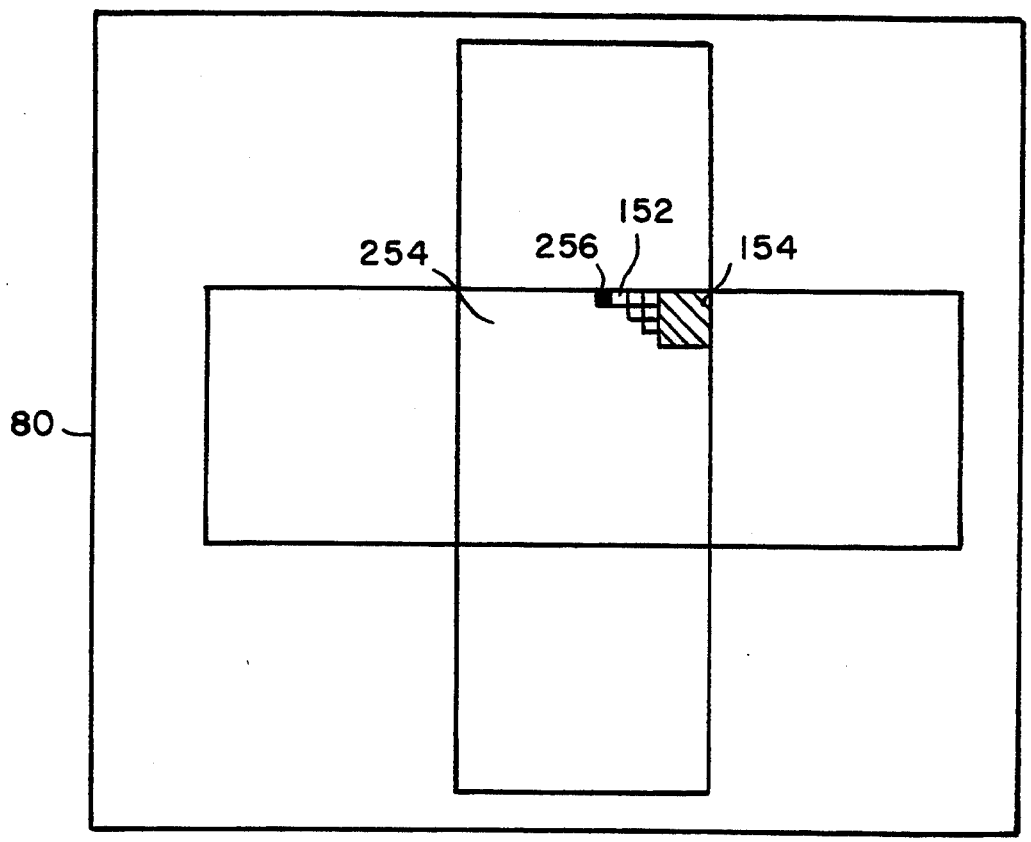
FIG. 12 is an illustration of a suitable display for use in conjunction with the present invention.

To assist in the sampling process, the user may be guided by a display 80 which may look similar to the display shown in FIG. 12. FIG. 12 is a planar projection of a reference surface on the display 80. A suitable reference surface is one which is easily projected onto a plane, and is one for which a human operator is readily able to visualize three-dimensionally, as surrounding the sampled object. Such a reference surface is shown in FIG. 13, with an illustrative object being shown in dashed lines.

Figure 13:
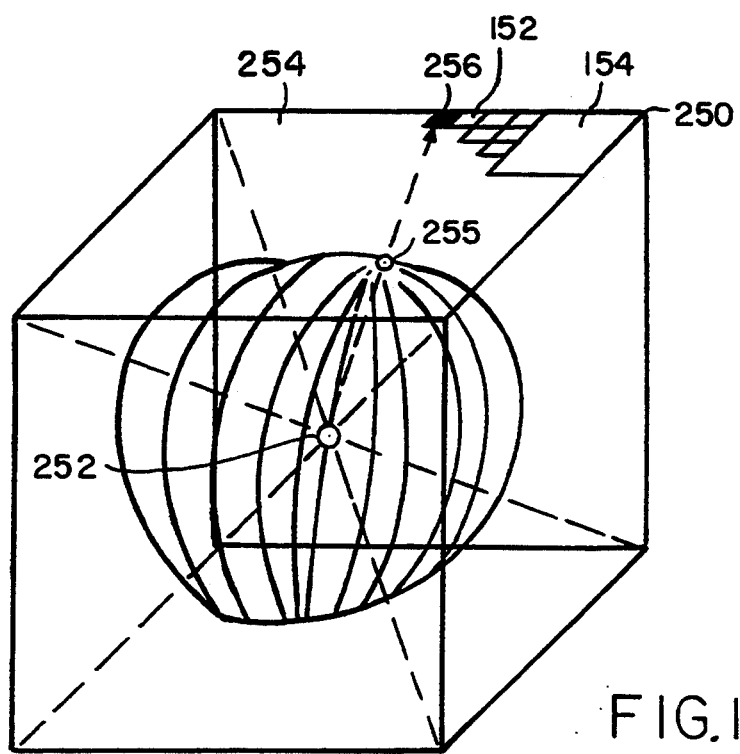
FIG. 13 is an illustration of a reference surface for assisting display.

FIG. 13 illustrates a cube 250 defined symmetrically about an origin 252, which represents the origin selected for the sampled object. The edges of the cube and the origin define six pyramids, each having a tip at the origin and a base which is a face of the cube. Any sample point obtained while sampling an object may be projected onto one of these faces. A face may be displayed on display 80, such as face 254. Because a mapping is known between the face and the display coordinates, and because a mapping is known between a given sample point and a given face, a sample point may be readily displayed on display 80. For example, point 255 on the object surface may be projected to a cell 256 on a face of the cube 250. This cell 256 may be projected on display 80, as shown in FIG. 12. A cursor or other type of indicator can be placed at this location on the display on the reference surface thereby indicating to the user the location of the probe tip.

The display 80 can also be used to indicate what regions of the sampled object need to be further sampled, in a manner to be described in more detail below. With such a display, a user can guide the probe tip to regions of the reference surface which refer to regions of the object surface which need more sampling. Thus, the sampling process may be guided in an efficient manner.

Figure 14:
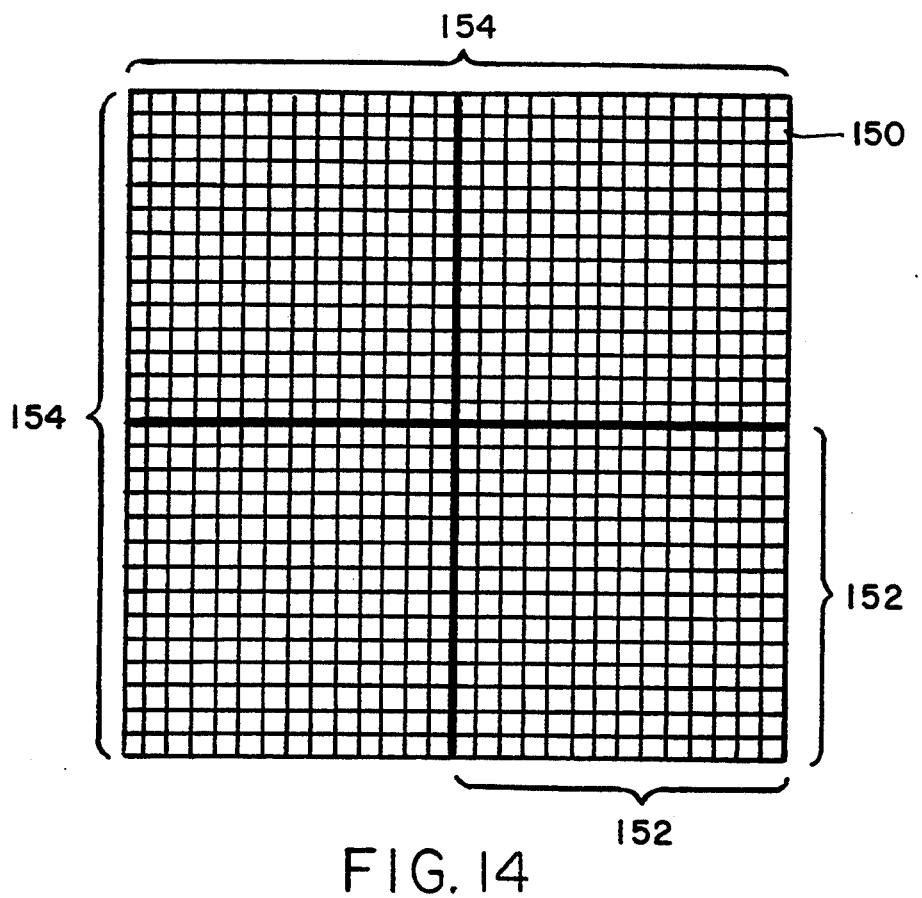
FIG. 14 is an illustration of the divisions of a reference surface for use in determining the adequacy of sampling.

The determination of the adequacy of sampling, and its relation to the display 80 and reference surface, will now be described in connection with FIGS. 14–17. FIG. 14 illustrates a portion of a reference surface divided into a number of cells 150. These cells are grouped into sectors such as sector 152. A sector 152 may contain as few as one cell 150. The number and size of cells 150 on the reference surface is based on the desired precision of measurement at the surface of the object. That is, if the desired spacing of sample points is 25 microns, the cells are sized so that their projection on the surface of the object is 25 microns or less. These sectors 152 are further grouped into regions 154. These divisions are also shown on the display 80 illustrated in FIG. 12.

The sectors 152 need not be the same shape as the face, nor need they be the same size everywhere on the face. If, as is the case with the dental digitizer, a different density of sample points may be preferable in one direction than in another, the sectors 152 and cells 150 may be made rectangular.

One way of achieving non-uniform density of sample points is to have a face divided into cells 150 spaced at the lowest required density. Where higher density is required, a sector 152 becomes a set of, for example, four cells 150. A sector 152 with a number of cells 150 does not "improve" until two or more cells 150 improve. What is meant by improvement will be described in more detail below. A sector 152 with two or more cells 150 is treated as any other sector 152, except that it is harder to "improve".

The ideal size of a region 154 allowing rapid and accurate sampling is strongly dependent on surface and shape characteristics of the object, the sampling technique used by the digitizer operator, etc. A region 154 is subdivided so that a sufficient count of sectors 152 exists, typically greater than 3×3. Optimal sector and cell count in a region 154 is once again job and operator-dependent. The number of regions, number of sectors, number of cells, and their size and shape are dependent on both task and operator characteristics and can be varied accordingly.

A region 154 may be considered to be adequately sampled when a sufficient number of cells 150 have points on the surface of the sampled object. To determine whether this is the case, a sum S is assigned to each region 154. This sum S represents the sum of all of the distances stored for each cell 150 in a region 154. Each distance is initialized to some value "BIG" which is greater than the sum which would be registered if all sampled points were at the limit of the probe sampling range. Thus the sum S for each region is even larger. If each cell contains one actual sample point, the sum S will be less than "BIG".

The data structures used to store the sum S for a region 154 and a distance for a sample point in cell 150 are separate from data structures for storing sampled points on the basis of direction. The structures may be implemented, however, in a similar way.

Figure 15:
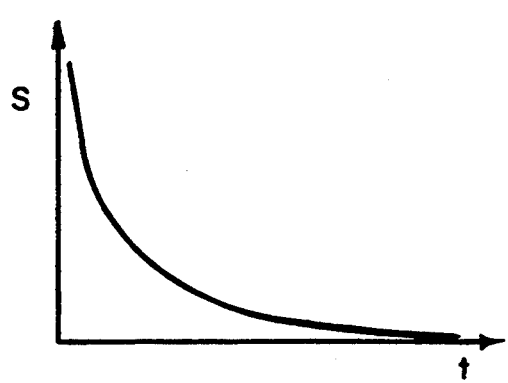
FIG. 15 is a graph illustrating how a sum of distances for a region decreases over time.

Every time a new sample point is obtained in a cell 150, the sum S for the region containing that sample is reduced by the amount of improvement obtained by the new sample point. A sector 152 is considered "improved" when a sample 150 which it contains is improved by the acquisition of an improved sampled point. As more sample points are obtained for a region 154, the sum S decreases with respect to time in a manner as shown in FIG. 15. Thus, the rate of change of the sum S with respect to time decreases and eventually becomes negligible as the sample point set matches the true surface more and more closely. When the rate of change of the sum S is sufficiently low, continued sampling will obtain little improvement. Thus, it can be said that the data is adequate when this rate of change is sufficiently small.

In order to determine the rate of change of the sum S, a measure of time needs to be adopted. This measure of time should be based on whether improved sample points are obtained in a cell 150, or sector 152, in a region 154, rather than on real time, because it is possible that a region 154 will have no sample points during some periods of real time during sampling. Furthermore, the measure of time should require improved points to be obtained spread out throughout a region 154 rather than concentrated in a small area of the region.

Figure 16:
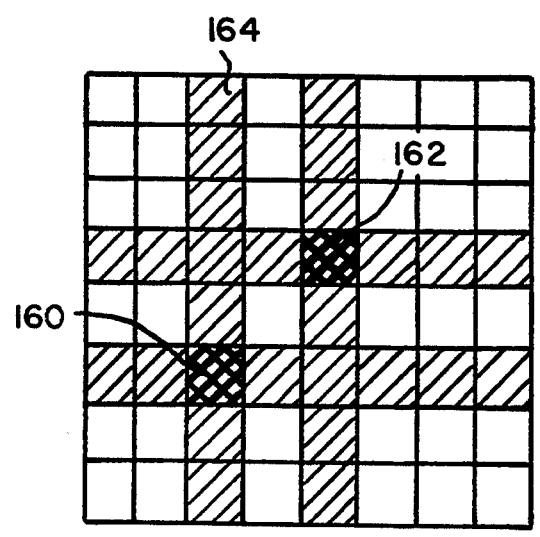
FIG. 16 is a diagram representing a data structure for determining the adequacy of sampling.

One possible timing method will now be described in connection with FIG. 16. With this method, a count of time is measured according to a number of new points obtained, but following a couple of constraints. These constraints can be represented graphically as shown in FIG. 16, and may be understood as analogous to "Rook's moves" in chess. An improved point is first acquired in a sector 152 of a region 154, such as sector 160. One count of time is thus obtained. A second point which may further the counting process is any improved point in any sector 152, except a sector in the same row or column of any previously counted point. Thus, a point in sector 162 would be acceptable for incrementing a time counter, but one in sector 164 would not. Any subsequent improved point may not be in the same column or row as sectors 160 or 162. Evidently, the accumulation of new points becomes increasingly difficult. If the region contains N by N sectors, more than N/2 new points would be very difficult to obtain. In order to insure that each sector of a region gets at least one sample point during the sampling process, the first period of time counted only occurs after each sector receives one point. This constraint is achieved when the sum S for a region is less than the large value "BIG". Thus, when, for example N/2 points have been obtained, this may represent one time division for the rate of change calculation.

Figure 17:
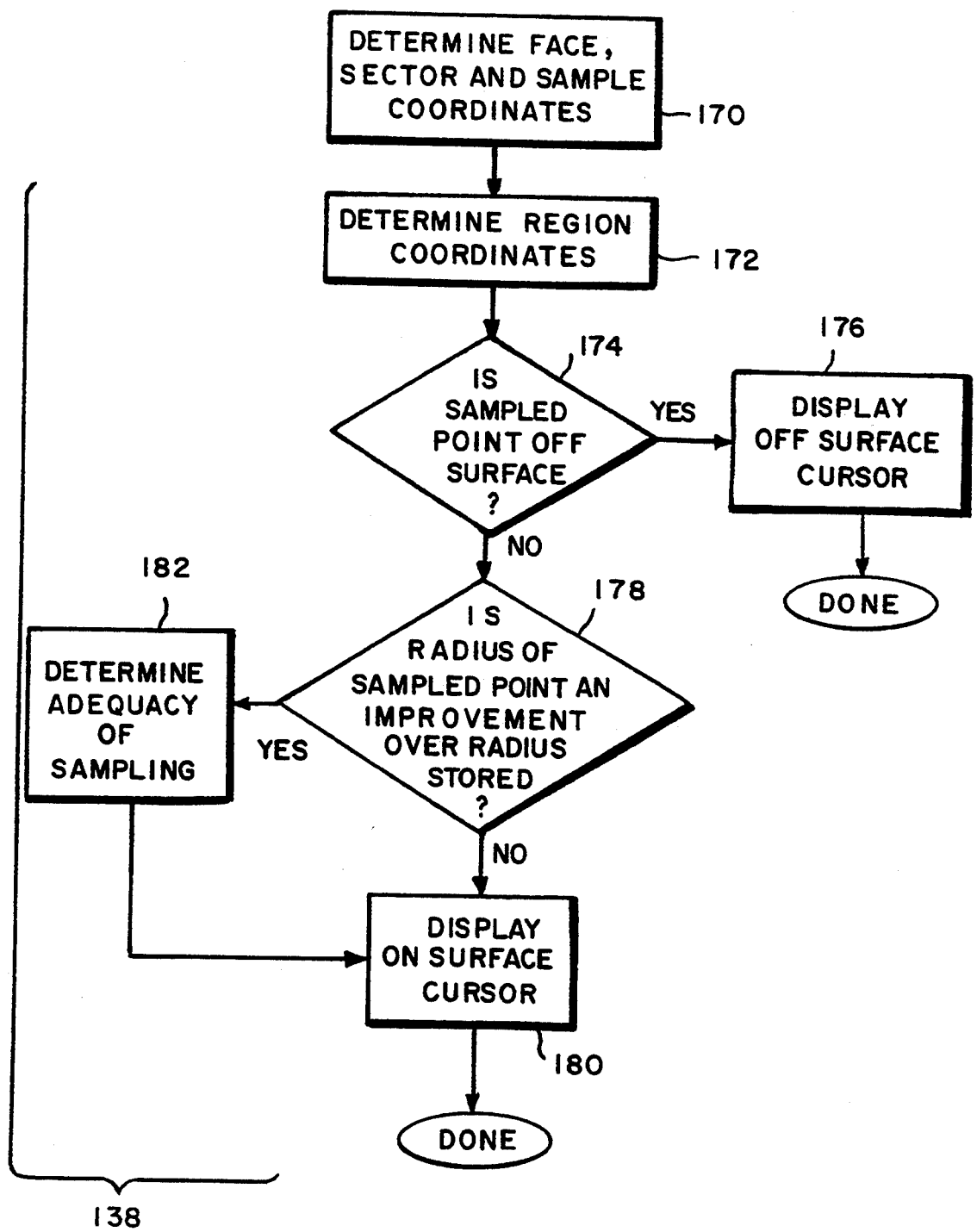
FIG. 17 is a flowchart describing how a sample point is displayed.
Figure 18:
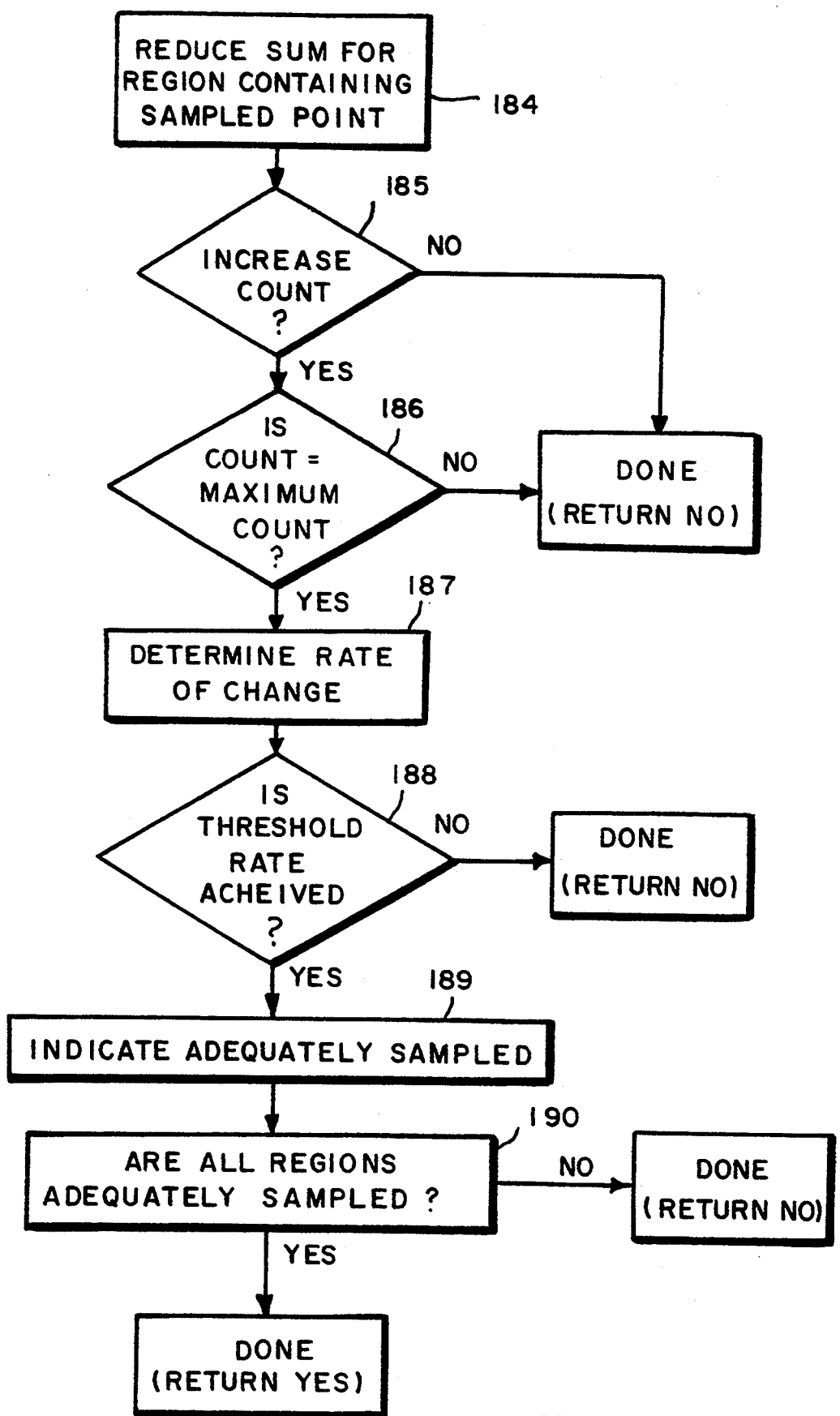
FIG. 18 is a flowchart describing how the adequacy of sampling is determined and conveyed to the user.

The implementation of the display and the determination of adequacy, as described above, will now be further illustrated in connection with the description of FIGS. 17 and 18.

In order to display a point, represented by Cartesian or spherical coordinates, the face of the reference surface, sector, sample and region coordinates within that face need to be determined (steps 170 and 172).

These steps 170 and 172 assume that appropriate data structures have been allocated to represent each face for the reference surface. That is, for each face, a number of sectors, regions and sectors per region are defined. For each region, memory space is allocated for: a time counter, which is initialized to zero; a status indicator for indicating adequacy of sampling in that region which is initialized to a value indicating inadequate sampling; a sum S initialized to the number of sectors per region multiplied by a very large radius value; a previous sum, which is initialized to the initial radius sum S; a timing array representing the number of sectors along the X axis region, initialized to all zeros or other constant; and timing array for the Y axis of the region. These arrays are used in connection with the timing procedure described above in connection with FIG. 16. These data structures may be allocated for each region as part of an array, which array is addressable by a value representing the face on which the region is located, and the X and Y coordinates of the region in the face.

A similar array is used to store information for each sector. For each sector, memory space is allocated for: the best radius pointing to that sector, which is initialized to a very large value; and the azimuth and elevation for this best radius. These azimuth and elevation values are the indices to the main data storage array described above for the data sampling procedures.

With the appropriate data structures and constants initialized, the face, sector, cell and region coordinates for a given point may be determined. The following procedures may be used for sample points in Cartesian coordinates (x, y, z) and when a cubic reference surface is used.

To determine whether a point (x, y, z) lies on the top face or bottom face of the cube (plaines of constant z), the following procedure is followed.

(1) if the absolute value of z/x is greater than 1, and the absolute value of z/y is greater than 1, then the projected point lies either on the top face or the "bottom face"—the bottom plane of the cube. if $z >= 0$ then the point is projected onto the top face—otherwise to the bottom face.

If the point is neither on the top face nor the bottom face, it must be on one of the "side" faces. For clarity, the four remaining faces are called "x+" (the face with all positive x values) and similarly "x−", "y+", "y−". Thus, (2) if $x>0$ and the absolute value of x/y is greater than 1 then the projected point lines on "x+"

(3) if $x<0$ and the absolute value of x/y is greater than 1 then the projected point lines on "x−".

Points which fail both of these tests lie on either "y+" or "y−"

(4) if $y>0$ then the projected point lines on "y+", else the projected point lines on "y−"

When it is determined on which face a point is projected, the x and y coordinates of the sector containing the sampled point, are calculated with respect to the determined face. (These x and y coordinates are different from the x, y and z coordinates of the sample with respect to the origin).

The coordinates of the containing sector of the face are determined by a similar "logical chain" as that used above for choosing the face. One of the reasons for choosing a cube as the reference surface is that the process is easy to describe and program, but the process is readily generalized to other surfaces such as cylinders or polyhedra.

This process will be described in connection with a point which is projected onto the "x+" plane. This projection may be visualized as the intersection of the x+ plane with a line constructed through the origin (0,0,0) and the sampled point. For simplicity, it is assumed that each face of the reference surface is some unit length one (1) from the origin. Thus the x+ plane can be taken as the plane in space limited by the four orthogonal lines connecting the points (1,1,1,), (1,−1,−1), (1,1,−1), (1,−1,1). The x coordinate of the sector containing any point projected on the "x+" plane is 1. A projection conversion factor is then determined:

$$\text{factor} = \frac{1}{x}$$

where x is the x coordinate of the sample point. The y and z coordinates of the sampled point ($y_{face}$ and $z_{face}$), as projected on the face are:

$$y_{face} = \text{factor} \cdot y$$

$$z_{face} = \text{factor} \cdot z$$

where y and z are the coordinates of the sample point. The y and z coordinates with respect to the face of the sector containing the sampled point are:

$y_{sector}$ = integer value of ($y_{face}/c$)

$z_{sector}$ = integer value of ($z_{face}/c$)

where the face plane (of limited area) is divided into 2x(c-1) cells with y and z "addresses"($y_{sector}$ and $z_{sector}$) ranging from -(c-1) through 0 to (c-1). Similar calculations are made for points on other faces. This calculation simply determines the which pair of parallel lines (parallel to y=0), representing the box boundaries, between which the point lies.

In the case of a triangular face, for example, three sets of parallel lines would define "cells", and three calculations like those immediately above would need to be made. The defining equations would be less presentable, and the calculation a bit more demanding, but the principle would be the same.

Given the x and y coordinates with respect to the face of the sector, the region x and y coordinates with respect to the face may be determined in the following way:

$$\text{Region } x = \frac{\text{sector } x}{\text{\# of regions per } x \text{ side of face}}$$

$$\text{Region } y = \frac{\text{sector } y}{\text{\# of regions per } y \text{ side of face}}$$

These procedures assume that the regions and sectors are uniform in size. Adaptation may readily be made for non-uniform sizes from this teaching.

Other methods, such as using azimuth and elevation values, and methods for other reference surfaces, such as a cylinder or other polyhedra, may be used as should be apparent to those of ordinary skill in this art.

When the coordinates on the reference surface are determined, processing continues with step 174 of determining whether the sample point is on the surface. This step is performed by examining the flag which is set in step 143 or 154 of FIG. 11. If the sample point is off the surface of the object, a cursor is displayed on the determined sector of the determined face in step 176. The cursor displayed should have a color or some other indication which is different from the cursor displayed when the sample point is on the surface of the object. After step 176, the process of displaying and determining the adequacy of sampling is completed.

If the sampled point is "on the surface" of the object, as indicated by the flag set in step 154, it is then determined, in step 178 if the radius of the sample point is an improvement over any radius stored in connection with the determined sector. If the sectors are divided into more than one cell, the radius is stored for each cell, however, the timing procedure remains based on the sector containing the sample point. In this manner it can be made more difficult to improve the sector by requiring improved sample points in a number of cells before the sector is improved. If the radius of the sample point is not an improvement, the location of the sample point is displayed on the reference surface on the display in accordance with the determined face and sector coordinates (step 180). Otherwise, the adequacy of sampling is determined in step 182 as will now be described in further detail in connection with FIG. 18.

The first step of determining adequacy of sampling is reducing the sum S for the region which contains the sampled point. (step 184). It is then determined whether the timing count should be increased in step 185. If the sum S is greater than the large value "BIG", sampling is inadequate, and this procedure terminates for this sampling point. For this purpose, the X and Y values of the sector with respect to the region are determined. The values stored in the x-axis and y-axis timing arrays, described above, are then set according to these x and y values. For example, if the improved sample point is at sector (3,2) of a region, the X axis timing array is set at element 3 to a value which indicates an improvement has been obtained, likewise the Y axis timing array is set at element 2. If one of the values at these elements in these arrays has already been set, the count is not increased. Otherwise, the count is increased.

If the count is not increased, sampling is not adequate and this procedure is terminated for the given sample point. Other sample points are then obtained. Otherwise, it is determined if the present count is equal to a maximum count, which is predetermined (step 186). Typically the maximum count is set to be half the number of sectors along one side of a region. If the present count is not the maximum count, sampling is not adequate and this procedure terminates for the given sample point. Otherwise, timing information (the count and timing arrays for the x and y axes for this region) is reset, and the rate of change of the sum S is determined in step 187.

The rate of change of the sum S is determined by the difference between the previous sum stored, and the current sum S. The previous sum can now be set to the current sum S. It can then be determined in step 188 whether a threshold rate has been achieved. That is, the rate of change determined in step 187 is compared to some predetermined threshold value, and if the determined rate of change is sufficiently low, it can be indicated (in step 189) that this region has been adequately sampled. Otherwise, sampling is not adequate for this region and the procedure terminates.

The indication that a region is adequately sampled can be provided by displaying an appropriate color, or grey scale, on the display for that region, such as is shown at region 154 in FIG. 12. If this region is not adequately sampled, it is possible to indicate on the display whether or not a sector has been sampled, such as sector 152 in FIG. 12.

When it has been indicated that a region has been adequately sampled in step 189, it can then be determined whether all regions or a sufficient number of regions have been adequately sampled in step 190. This step may be performed by the operator, merely by examining the display 80. The computer may also perform this determination by examining the status of each region. By determining the adequacy of a sample in the foregoing manner, it ensures that enough points are available for modeling. That is, sampled points which are critical to the correct modeling of the sampled object are obtained. Moreover, this method insures that the operator will not be delayed by sampling points which are not necessary, and will be directed to sampled points which are important. Moreover, it provides a display which demonstrates to an operator how well sampling is progressing.

In some instances, the data obtained through the sampling process may include bad data points. With the procedures as described above, however, the number of bad data points is typically sufficiently small and of low density. Thus, it is possible to filter the data set on a point-by-point basis to eliminate bad data points. Step 144 (FIG. 11) can be performed for each data point in a data set. A poor data point is simply rejected and replaced with some "null" value.

When it has been determined that sampling is adequate, the sampling data retained in the main data set, as constructed during the process described above in connection with FIG. 11, may be used for input into a solids modeling program, may be output to a secondary memory, or may be used with other application programs such as machine generation of a die or prosthesis.

Having now described an embodiment of the invention, it should be apparent to those skilled in the art that the foregoing is illustrative only and not limiting, having been presented by way of example only. Numerous other embodiments and modifications thereof are contemplated as falling within the scope of the present invention as defined by the appended claims and equivalents thereto.

What is claimed is:

1. A system for obtaining a digitized representation of a surface of an object, comprising:

a probe, having a base and a tip for probing the surface of the object, for obtaining a sequence of electrical signals, indicative of the location of the tip in a reference coordinate system, at a given sampling rate;

means for maintaining the base of the probe and the object in a fixed spatial relationship;

means responsive to the sequence of electrical signals from the probe for providing a corresponding sequence of digital signals indicative of the electrical signals;

a memory for storing information indicative of the digital signals;

means, responsive to the sequence of digital signals, for defining a reference surface and an origin with reference to the object;

means, responsive to each tip position indicated by the sequence of digital signals, for projecting the tip position onto a subregion of the reference surface, and for determining the distance of the tip from the origin, and for replacing, in the memory, any previously stored distance for the subregion with the determined distance when the determined distance is less than the previously stored distance for the subregion;

means, responsive to the means for determining, for determining whether enough tip positions have been obtained;

a display, responsive to the sequence of digital signals, for indicating the position of the probe tip with reference to the reference surface.

2. The system of claim 1 wherein the probe comprises a plurality of linkages which are interconnected at a plurality of joints wherein at least three joints each have a corresponding sensor which provides an electrical signal which is indicative of the angle of the joint.

3. The system of claim 2, wherein the sensor is a Hall effect sensor.

4. The system of claim 2, wherein the sensor is a potentiometer.

5. The system of claim 2, wherein the sensor is a capacitive sensor.

6. The system of claim 2, wherein the sensor is an angular resolver.

7. The system of claim 2, wherein the sensor is an optical encoder.

8. The system of claim 1, wherein the reference coordinate system is a Cartesian coordinate system.

9. The system of claim 1, wherein the reference coordinate system is a spherical coordinate system.

10. A method for sampling the surface of an object, comprising the steps of:

affixing a probe in a position fixed relative to the object, the probe providing a position signal corresponding to a position of a tip of the probe in a reference coordinate system;

selecting an origin for the probe with reference to the object;

probing said object with the tip of the probe to obtain a sequence of position signals;

determining a distance from the selected origin to the tip of the probe for said position signals;

storing only improved points in a memory according to the determined distance and the position of the tip of the probe;

determining when an adequate number of samples has been taken; and periodically displaying the position of the tip of the probe and an indication of the adequacy of sampling to a user.

11. The method of claim 10, wherein the origin selected in the step of selecting an origin for the probe is such that the distance from any point on the surface of the object to the origin in any direction of interest is shorter than the distance from any point to the origin in the same direction which is not on the surface of the object.

12. The method of claim 10, further comprising the step of performing error rejection procedures.

13. The method of claim 12, wherein the step of performing error rejection procedures includes the step of comparing the distance determined for a position signal for one direction to previously obtained distances of position signals for similar directions.

14. The method of claim 12, wherein the step of performing error rejection procedures includes the step of determining whether a position signal indicates a position which is within a minimum coordinate value and a maximum coordinate value.

15. The method of claim 14, wherein the maximum and minimum values in the error rejection procedure are obtained from characteristic locations used to select an origin.

16. The method of claim 10, wherein the origin selected in the step of selecting an origin is such that the origin is located in a region through which no tangent line to the surface of the object passes.

17. The method of claim 10, wherein the step of selecting an origin includes step of selecting a set of points as an origin set, and wherein the step of determining a distance for each position signal includes the step of determining the least distance between the position defined by a position signal and the origin set of points.

18. The method of claim 10, wherein characteristics of the object to be sampled are relatively unknown and wherein the step of selecting an origin comprises the steps of accepting a plurality of sample points and continuously calculating an origin until sufficient sample points have been acquired.

19. The method of claim 10, wherein characteristics of the object to be sampled are predetermined, and the step of selecting an origin include sampling a characteristic location on the object using a probe and calculating the origin on the basis of the characteristic locations.

20. The method of claim 19, wherein the object is a tooth prep for which a crown is to be prepared, and wherein the characteristic location includes the center of the top of the tooth prep and margin points of the tooth prep.

21. The method of claim 10, wherein the object is a tooth prep, and the method further comprises the steps of sampling interproximal and occlusal surfaces.

22. The method of claim 21, wherein the step of sampling occlusal surfaces includes the step of creating an impression of a mating tooth of the tooth prep using an amorphous material.

23. A data processing system for obtaining a three dimensional representation of an object with complex and unique geometry, using a sampling probe having a tip for tracing the surface of the object, the system comprising:
  means for receiving electrical signals indicative of the position of the tip of the probe in a reference coordinate system;
  means, responsive to the means for receiving, for determining an origin with reference to the object;
  means for storing a plurality of distances, each distance corresponding to a given direction from the origin, the means for storing being addressable by the directions to store and to retrieve the corresponding distances;
  means, responsive to a signal received by said means for receiving, for determining the direction and distance of the tip of the sampling probe with reference to the origin;
  means for comparing the distance determined to any distance stored in the means for storing corresponding to the determined direction and for storing the determined distance in the means for storing when the determined distance is less than any stored distance.

24. The data processing system of claim 23, further comprising means for displaying the position of the tip of the sampling probe as projected on a reference surface which surrounds the origin.

25. A data processing system for obtaining a digitized representation of a surface of an object, comprising:
  a memory in which an application program defined by a plurality of program steps stored;
  a central processor;
  a bus connecting the memory to the processor;
  the central processor controlling data flow and data manipulation by executing program steps of the application program;
  a probe input system which receives electrical signals from a probe having a tip which electrical signals are indicative of a position of the tip of the probe in a reference coordinate system;
  wherein the central processing unit, while executing the program steps, acts as a:
    means, responsive to signals received by the probe input system, for defining a reference surface and an origin with reference to the objects;
    means, responsive to each tip position indicated by the sequence of electrical signals, for projecting the position onto a subregion of the reference surface, and for determining the distance of the tip from the origin, and for replacing, in the memory, any previously stored distance for the subregion with the determined distance when the determined distance is less than the previously stored distance for the subregion;
    means, responsive to the means for determining, for determining whether enough tip positions have been obtained; and
    means, for indicating to a user the tip position with reference to the reference surface.

26. The system of claim 25, wherein the probe input system includes an analog-to-digital converter which operates at a sampling rate which is different from a rate at which the central processor operates, and includes a register which operates at a rate defined by the rate at which the computer is operating.

27. The data processing system of claim 25, further comprising a calibration and conversion processor which converts digital signals obtained from the probe input system to coordinate values in a reference coordinate system.

28. The system of claim 27, wherein the calibration and conversion processor is defined by program steps stored in memory as executed by the central processor to calculate a polynomial function.

29. The system of claim 27, wherein the calibration and conversion processor is defined in the memory, by a look-up table and may be accessed according to the electrical signals obtained from the probe input system.

30. A method for sampling the surface of an object, comprising the steps of:
  affixing a probe in a location having a fixed spatial relationship with the object, the probe providing a position signal corresponding to a position of a tip of the probe in a reference coordinate system;
  selecting an origin with reference to the object such that the distance from any point on the surface of the object to the origin in any direction of interest is shorter, than the distance from any point to the origin in the same direction which is not on the surface of the object;
  probing the object with the tip of the affixed probe to obtain a sequence of position signals;
  determining a distance from the selected origin of the probe for each of said position signals; and
  projecting the tip position onto a subregion of the reference surface; and
  replacing in a memory any previously stored distance for the subregion with the determined distance when the determined distance is less than the previously stored distance for the subregion.

31. A method for sampling the surface of an object, comprising the steps of:
  affixing a probe in a location having a fixed spatial relationship with the object, the probe providing a position signal corresponding to a position of a tip of the probe in a reference coordinate system;
  selecting an origin with reference to the object such that the distance from any point on the surface of the object to the origin in any direction of interest is shorter than the distance from any point to the origin in the same direction which is not on the surface of the object;
  probing the object with the tip of the affixed probe to obtain a sequence of position signals;
  storing a plurality of distances, each distance corresponding to a given direction from the origin;
  determining a distance and a direction from the selected origin of the probe for each of said position signals; and
  comparing the determined distance to any stored distance for the determined direction and storing the determined distance when the determined distance is less than any stored distance.

* * * * *